United States Patent
Day et al.

(10) Patent No.: US 10,829,606 B2
(45) Date of Patent: Nov. 10, 2020

(54) SURFACE MODIFIED POLYMER COMPOSITIONS

(71) Applicant: Lubrizol Advanced Materials, Inc., Cleveland, OH (US)

(72) Inventors: Roger W. Day, Solon, OH (US); Hua Zhang, Cottonwood Heights, UT (US); Umit G. Makal, Stow, OH (US); Richard Woofter, Medina, OH (US); Kiara Smith, Mayfield Heights, OH (US)

( * ) Notice: Subject to any disclaimer, the term of this patent is extended or adjusted under 35 U.S.C. 154(b) by 0 days.

(21) Appl. No.: 15/567,711

(22) PCT Filed: Apr. 22, 2016

(86) PCT No.: PCT/US2016/028814
§ 371 (c)(1),
(2) Date: Oct. 19, 2017

(87) PCT Pub. No.: WO2016/172460
PCT Pub. Date: Oct. 27, 2016

(65) Prior Publication Data
US 2018/0105665 A1    Apr. 19, 2018

Related U.S. Application Data

(60) Provisional application No. 62/251,791, filed on Nov. 6, 2015, provisional application No. 62/152,391, filed on Apr. 24, 2015.

(51) Int. Cl.
| | |
|---|---|
| *C08F 2/44* | (2006.01) |
| *C08J 7/16* | (2006.01) |
| *A61L 27/34* | (2006.01) |
| *A61L 29/08* | (2006.01) |
| *A61L 31/10* | (2006.01) |
| *C08G 71/04* | (2006.01) |
| *C08G 77/04* | (2006.01) |
| *C08G 81/02* | (2006.01) |
| *C08J 3/20* | (2006.01) |
| *B29C 71/02* | (2006.01) |
| *C08K 5/01* | (2006.01) |
| *C08K 5/02* | (2006.01) |
| *C08K 5/101* | (2006.01) |
| *C08K 5/19* | (2006.01) |
| *C08K 5/20* | (2006.01) |
| *C08L 23/08* | (2006.01) |
| *C08L 27/12* | (2006.01) |

(52) U.S. Cl.
CPC .............. *C08J 7/16* (2013.01); *A61L 27/34* (2013.01); *A61L 29/085* (2013.01); *A61L 31/10* (2013.01); *C08F 2/44* (2013.01); *C08G 71/04* (2013.01); *C08G 77/04* (2013.01); *C08G 81/025* (2013.01); *C08J 3/20* (2013.01); *C08J 7/08* (2013.01); *C08K 5/01* (2013.01); *C08K 5/02* (2013.01); *C08K 5/101* (2013.01); *C08K 5/19* (2013.01); *C08K 5/20* (2013.01); *C08L 23/08* (2013.01); *C08L 27/12* (2013.01)

(58) Field of Classification Search
CPC ........................................................ C08J 7/16
See application file for complete search history.

(56) References Cited

U.S. PATENT DOCUMENTS

| | | | | |
|---|---|---|---|---|
| 3,728,151 A | * | 4/1973 | Sherman et al. | C08F 293/00 442/80 |
| 3,995,085 A | * | 11/1976 | McCown | C08F 220/24 442/94 |
| 6,090,901 A | * | 7/2000 | Bowers | C08F 230/02 526/277 |
| 6,207,777 B1 | * | 3/2001 | Shimada | D06M 15/263 526/245 |
| 6,268,440 B1 | * | 7/2001 | Kudo | C09D 183/10 524/588 |
| 6,287,707 B1 | * | 9/2001 | Luthra | A61L 27/16 428/522 |
| 8,318,867 B2 | | 11/2012 | Mullick et al. | |
| 2003/0097120 A1 | * | 5/2003 | Santerre | A61L 33/0017 604/891.1 |
| 2009/0211968 A1 | * | 8/2009 | Ho | D01F 1/10 210/507 |
| 2010/0069946 A1 | * | 3/2010 | Cromack | A61L 29/085 606/192 |
| 2011/0207841 A1 | * | 8/2011 | Kosar | B01D 71/34 521/134 |
| 2012/0136087 A1 | * | 5/2012 | Parakka | A61L 15/26 523/107 |
| 2012/0148774 A1 | * | 6/2012 | Mullick | C08G 18/227 428/36.9 |
| 2013/0178125 A1 | * | 7/2013 | Jiang | C09D 5/165 442/1 |
| 2013/0183262 A1 | * | 7/2013 | Wynne | C08G 65/18 424/78.3 |

FOREIGN PATENT DOCUMENTS

| | | |
|---|---|---|
| EP | 1418946 B1 | 9/2007 |
| WO | 2007/08514 A2 | 1/2007 |
| WO | 2010147779 A2 | 12/2010 |

* cited by examiner

*Primary Examiner* — Mark S Kaucher
(74) *Attorney, Agent, or Firm* — Thoburn Dunlap; Teresan Gilbert

(57) ABSTRACT

A surface-modified polymer composition formed from an oligomeric or polymeric additive and a base polymer is disclosed. The surface-modified polymer provides non-fouling and/or non-thrombogenic properties. The composition is particularly useful in articles and materials for medical applications.

22 Claims, No Drawings

SURFACE MODIFIED POLYMER COMPOSITIONS

CROSS REFERENCE TO RELATED APPLICATION

This application claims priority from PCT Application Serial No. PCT/US2016/028814 filed on Apr. 22, 2016, which claims the benefit of U.S. Provisional Application No. 62/251,791 filed on Nov. 6, 2015 and U.S. Provisional Application No. 62/152,391 filed on Apr. 24, 2015, both of which are incorporated in their entirety by reference herein.

FIELD OF THE INVENTION

There is provided a surface-modified polymer composition which includes an oligomeric or polymeric additive and a base polymer. The additive can include one or more of a bloom-promoting, non-fouling or adherence-promoting monomer. The polymer composition provides a non-protein fouling and/or non-thrombogenic surface. The polymer composition may find use in medical devices where non-fouling and/or non-thrombogenic characteristics are of particular importance.

BACKGROUND

In recent decades, numerous medical devices have been developed which have improved medical treatment and enhanced patient lives. The performance of the medical devices, in many cases, are dependent on the surface properties of the biomaterials.

Implantation of a medical device into a patient's body can result in various reactions to the device. Introduction of a material into contact with the blood generally causes coagulation and thrombosis. Additionally, the introduction of a material into a human body results in activation of the body's immune response, leading to acute and sometimes chronic inflammation.

As such, much emphasis has been placed on the modification of the surfaces of biomaterials, in particular the surface modification of polymers, to decrease or eliminate the surface adsorption of proteins and improve their biocompatability. Common approaches to surface modification of polymers has included plasma polymerized surfaces, surface coatings, grafting of polymers from or to the surface, and physical adsorption of surface modifying materials onto a polymer surface. Each of these methods, however, has significant drawbacks, including expense, difficulty of application to devices with intricate surface geometries, and imparting relatively fragile surface films.

Thermoplastic polyurethanes (TPUs) are widely used as biomaterials owing to their excellent physical and mechanical properties. Surface modification of TPUs for biomedical applications has previously been accomplished by a variety of means, including coating the surface via dip coating or spray coating, or plasma polymerization of appropriate materials onto the surface of the TPU. Further, the addition of additives, such as fluorocarbons, which are non-compatible with the TPU and spontaneously migrate to the polymer surface, have been used to modify the polymer surface. Fluorocarbon surfaces, however, do not prevent fouling by proteins.

It would be desirable, then, to provide a surface-modified polymer having non-fouling and/or non-thrombogenic characteristics without post treatment following manufacture of the devices.

SUMMARY

The disclosed technology provides a surface-modifying additive composition including an oligomeric or polymeric additive formed from two or more of i) a zwitterionic monomer or a polyalkylene glycol monomer; ii) a silicone or fluorocarbon monomer, or combinations thereof; or iii) an alkyl substituted methacrylate, acrylate, acrylamide, or vinyl monomer, or combinations thereof.

The disclosed technology further provides surface-modifying additive composition in which the oligomeric or polymeric additive is a random, a block, a graft or a branched polymer or copolymer.

The disclosed technology further provides a surface-modifying additive composition in which the silicone or fluorocarbon monomer is present in the additive in an amount from 5 wt % to 40 wt % of total monomer composition.

The disclosed technology further provides a surface-modifying additive composition in which the silicone monomer comprises a functionalized polysiloxane.

The disclosed technology further provides a surface-modifying additive composition in which the zwitterionic monomer is present in an amount from 10 wt % to 40 wt % of the total monomer composition.

The disclosed technology further provides surface-modifying additive composition in which the zwitterionic monomer comprises a phosphorylcholine, a carboxybetaine, or a sulfobetaine monomer.

The disclosed technology further provides a surface-modifying additive composition in which the fluorocarbon monomer includes a functionalized fluorocarbon.

The disclosed technology further provides a surface modifying additive composition in which the polyaklyene glycol monomer is present in an amount from 10 wt % to 50 wt % of the total monomer composition.

The disclosed technology further provides a surface-modifying additive composition in which the polyalkylene glycol monomer is a monomethyl polyethylene glycol methacrylate.

The disclosed technology further provides a surface-modifying additive composition in which the alkyl or other substituted methacrylate, acrylate, acrylamide or vinyl monomer is present in an amount from 10 wt % to 70 wt % of the total monomer composition.

The disclosed technology further provides a surface-modifying additive composition in which the alkyl or other substituted methacrylate, acrylate, acrylamide or vinyl monomer comprises methyl methacrylate.

The disclosed technology further provides a surface-modifying additive composition in which the phosphorylcholine monomer comprises 2-hydroxyethyl methacrylate phosphorylcholine.

The disclosed technology further provides a surface-modifying additive composition in which the additive composition has a molecular weight (Mn) of from 1000 to 50,000 daltons.

The disclosed technology further provides a surface-modifying additive composition in which the additive composition provides a reduction in protein absorption of at least 50 percent, or at least 60 percent, or at least 70 percent.

The disclosed technology further provides a surface-modifying additive composition in which the additive composition is melt processable or solution processable.

The disclosed technology further provides a surface-modified polymer composition including the surface modifying additive composition and a base polymer.

The disclosed technology further provides a surface modified polymer composition in which the surface-modifying additive composition is added to the base polymer to form a blend.

The disclosed technology further provides a surface modified polymer composition in which the base polymer comprises a nylon, a polyethylene, a polyester, a thermoplastic polyurethane, a polyvinylchloride, a polysulfone, a polysiloxane, a polypropylene, a polycarbonate, a polyether sulfone, a polyether ether ketone, a polylactide (PLA) polymer, a polylactide-co-glycolide (PLG) polymer, a polycaprolactone polymer, a polydioxanol polymer, a poly(1,3-trimethylene carbonate) polymer, a polytyrosine carbonate polymer, a polyacrylate, a polymethacrylate, polylactic acid, polyglycolic acid, and combinations thereof.

The disclosed technology further provides a surface modified polymer composition in which the base polymer comprises thermoplastic polyurethane.

The disclosed technology further provides a surface modified polymer composition further including one or more additional thermoplastic polyurethanes to form a thermoplastic polyurethane blend.

The disclosed technology further provides a surface modified polymer composition in which the surface modified polymer composition is non-protein fouling, non-thrombogenic, or combinations thereof.

The disclosed technology further provides a surface modified polymer composition in which the surface modifying additive composition is present in the polymer composition in an amount from 0.1 wt % to 10 wt %.

The disclosed technology further provides a method of making a surface-modified polymer composition, including a) forming an oligomeric or polymeric additive comprising i) a zwitterionic monomer, or a polyalkylene glycol monomer; ii) a silicone or fluorocarbon monomer, or combinations thereof; or an alkyl substituted methacrylate, acrylate, acrylamide, or vinyl monomer, or combinations thereof; and b) incorporating the additive into a base polymer.

The disclosed technology further provides a method in which incorporating of the additive comprises melt processing of the additive into the base polymer or addition of the additive during synthesis of the polymer.

The disclosed technology further provides a method further including annealing the polymer composition.

The disclosed technology further provides a method in which the annealing is performed at a temperature of from about the glass transition temperature of the base polymer up to about the melting point of the base polymer.

The disclosed technology further provides method in which the annealing is performed at a temperature of from about 50° C. to about 150° C. for a period of from 2 hr up to about 7 days.

The disclosed technology further provides a method in which the base polymer comprises a nylon, a polyethylene, a polyester, a thermoplastic polyurethane, a polyvinylchloride, a polysulfone, a polysiloxane, a polypropylene, a polycarbonate, a polyether sulfone, a polyether ether ketone, a polylactide (PLA) polymer, a polylactide-co-glycolide (PLG) polymer, a polycaprolactone polymer, a polydioxanol polymer, a poly(1,3-trimethylene carbonate) polymer, a polytyrosine carbonate polymer, a polyacrylate, a polymethacrylate, polylactic acid, polyglycolic acid, and combinations thereof.

The disclosed technology further provides an article including a surface modifying polymer composition, the surface modifying polymer composition including a) an oligomeric or polymeric additive formed from two or more of i) a zwitterionic monomer or a polyalkylene glycol monomer; ii) a silicone or fluorocarbon monomer, or combinations thereof; or iii) an alkyl substituted methacrylate, acrylate, acrylamide, or vinyl monomer, or combinations thereof; and b) a base polymer; in which the oligomeric or polymeric additive is incorporated into the base polymer.

The disclosed technology further provides an article in which the polymer composition is coated onto a material forming the article.

The disclosed technology further provides an article in which the polymer composition is coated utilizing dip coating, roll to roll coating, spin coating or spray coating.

The disclosed technology further provides an article in which the coating is applied at a thickness from 1 micrometer to 200 micrometers.

The disclosed technology further provides an article in which the base polymer comprises a nylon, a polyethylene, a polyester, a thermoplastic polyurethane, a polyvinylchloride, a polysulfone, a polysiloxane, a polypropylene, a polycarbonate, a polyether sulfone, a polyether ether ketone, a polylactide (PLA) polymer, a polylactide-co-glycolide (PLG) polymer, a polycaprolactone polymer, a polydioxanol polymer, a poly(1,3-trimethylene carbonate) polymer, a polytyrosine carbonate polymer, a polyacrylate, a polymethacrylate, polylactic acid, polyglycolic acid, and combinations thereof.

The disclosed technology further provides an article in which the article comprises a medical device.

The disclosed technology further provides an article in which the medical device comprises one or more of an angiography catheter, an angioplasty catheter, a urology catheters, a dialysis catheter, a Swan-Ganz catheter, a central venous catheter, a peripherally inserted central catheter, a catheter connector, a dialysis membrane, medical tubing, a wound are article, and orthopedic article, a neural implant, a film, a drape, a biosensor, a dental implant, a heart valve, a heart by-pass machine, an extracorporeal blood device, a nerve conduit, a vascular graft, a stent, an implant or a contact lense.

The disclosed technology further provides an article in which the wound care article comprises one or more of a wound closure, a staple, a suture, a mesh, a buttressing device, a suture reinforcement, or a wound care dressing.

The disclosed technology further provides an article in which the orthopedic article comprises one or more of a nail, a screw, a plate, a cage, or a prosthetic.

The disclosed technology further provides an article in which the neural implant comprises one or more of a drain or a shunt.

The disclosed technology further provides an article in which the implant comprises one or more of an occular implant, a chochlear implant, or a breast implant.

The disclosed technology further provides an article in which the article is a personal care article, a pharmaceutical article, a health care product article, or a marine article.

The disclosed technology further provides a method of making the article including a) making a surface-modifying polymer composition; and b) forming the article.

The disclosed technology further provides a surface-modified polymer composition including a) an oligomeric or polymeric additive formed from i) a fluorocarbon monomer; and ii) a polydimethylsiloxane monomer; and b) a thermoplastic polyurethane.

DETAILED DESCRIPTION

Various preferred features and embodiments will be described below by way of non-limiting illustration.

The disclosed technology provides a surface modified polymer composition that includes a bloom-promoting monomer, a non-fouling monomer, an adherence-promoting monomer, and combinations thereof. In one embodiment, the polymer composition includes a) an oligomeric or polymeric additive formed from one or more of i) a phosphorylcholine, a carboxybetaine, a sulfo betaine or a polyalkylene glycol monomer; ii) a silicone or fluorocarbon monomer, or combinations thereof; and iii) an alkyl substituted monomer; and b) a base polymer.

The Oligomeric or Polymeric Additive

The surface-modified polymer composition as disclosed herein includes an oligomeric or polymeric additive formed from i) a zwitterionic monomer. In one embodiment, the zwitterionic monomer includes one or more of a phosphorylcholine, a carboxybetaine, a sulfobetaine, or a polyalkylene glycol monomer.

The additive of the invention can be oligomeric or polymeric. In one embodiment, the additive includes dimers, trimers, or tetramers. In one embodiment, the additive includes a block, a graft or a branched polymer or copolymer. In one embodiment, the oligomeric or polymeric additive has a molecular weight (Mn) of from 1,000 to 50,000 daltons. In one embodiment, the additive has a molecular weight of from 2,000 to 15,000 daltons.

The Zwitterionic Monomer

In one embodiment, the additive of the composition can include a non-fouling monomer. The non-fouling monomer can include a zwitterionic monomer or a polyalkylene glycol monomer. In one embodiment, the additive of the composition as disclosed herein includes a zwitterionic monomer or a polyalkylene glycol monomer. The zwitterionic monomer can include one or more of a phosphorylcholine, a carboxybetaine or a sulfobetaine monomer, derivatives thereof, or combinations thereof. Zwitterions are molecules that carry formal positive and negative charges on non-adjacent atoms within the same molecule. Both natural and synthetic polymers, containing zwitterion functionality, have been shown to resist protein adhesion. In one embodiment, the zwitterionic monomer includes a phosphorylcholine moiety, a sulfobetaine moiety, a carboxy betaine moiety, derivatives thereof, or combinations thereof. In one embodiment, the zwitterionic monomer includes 2-hydroxyethyl methacrylate phosphorylcholine.

The sulfobetaine monomer can be selected from one or more of sulfobetaine acrylates, sulfobetaine acrylamides, sulfobetaine vinyl compounds, sulfobetaine epoxides, and mixtures thereof. In one embodiment, the monomer is sulfobetaine methacrylate.

The carboxybetaine monomer can include carboxybetaine acrylates, carboxybetaine acrylamides, carboxybetaine vinyl compounds, carboxybetaine epoxides, and mixtures thereof. In one embodiment, the monomer is carboxybetaine methacrylate.

In some embodiments, the zwitterionic monomers incorporated into the oligomeric or polymeric additives are present in an amount from 10-40 mole percent of the total monomer composition of the additive.

The Polyalkylene Glycol Monomer

In one embodiment, the oligomeric or polymeric additive can further include a polyalkylene glycol monomer. In a further embodiment, the oligomeric or polymeric additive can alternatively include a polyalkylene glycol monomer, where the polyalkylene glycol monomer is utilized in place of the zwitterionic monomer. Suitable polyalkylene glycol monomers include, but are not limited to acrylate, methacrylate esters of polyether polyols having a total of from 2 to 100 carbon atoms. Useful commercial polyalkylene glycol monomers include poly(ethylene glycol) comprising ethylene oxide reacted with ethylene glycol or other alcohol, such as poly(ethylene glycol) methyl ether methacrylate/acrylate with various molecular weights, glycol butyl ether methacrylate/acrylate with various molecular weights, poly(ethylene glycol) methacrylate/acrylate with various molecular weights. In some embodiments, the polyalkylene glycol monomer can be present in an amount from about 10 mole % to about 50 mole % of the total monomer composition of the additive.

The Silicone or Fluorocarbon Monomer

The oligomeric or polymeric additive of the surface-modified polymer composition disclosed herein can include a bloom-promoting monomer. The bloom-promoting monomer can include a silicone or fluorocarbon monomer, or combinations thereof.

In one embodiment, the silicone monomer includes a functionalized polysiloxane. The functionalized polysiloxane can be mono- or multi-functionalized. Suitable examples of functionalized polysiloxane include mono- or multi-functionalized acrylate, methacrylate, vinyl or allyl functionalized polysiloxanes, such a mono vinyl terminated polydiemthylsiloxanes; mono methacryloxpropyl terminated polydimethylsiloxanes, vinyl terminated trifluoropropylmethylsiloxane; and monoallyl-mono trimethylsiloxy terminated polyethylene oxide. The polysiloxanes may generally have a molecular weight (Mn) of from 100 to about 100,000. The functional groups may be terminal, internal, or terminal and internal.

The functional polysiloxane may be represented by the following formula:

A-B-C wherein A is a polymerizable group selected from vinyl, acrylate, or methacrylate or an active hydrogen group selected from an alcohol, an amine or a thiol; B is an optional linking group, and C is a polysiloxane group.

Functionalized polysiloxanes which are useful in the additives of the invention are available commercially from a variety of sources. For example, terminally functionalized polysiloxanes are available from Evonik Industries under the Tegomer® range of products, including Tegomer® C-Si 2342 (Dicarboxyalkylpolydimethylsiloxane), Tegomer E-Si 2330 (Diepoxyalkylpolydimethyl siloxane), Tegomer® H-Si 2315 (Dihydroxyalkylpolydimethyl siloxane), and Tegomer® V-Si (Diacryloxypolydimethylsiloxane). Gelest Inc. also has various functional polysiloxane such as MCR-C12,18,22 series (MonoCarbinol Terminated polyDimethylsiloxane), MCR-C61,62 (MonoDiCarbinol Terminated PolyDimethylsiloxane), PDV series (Vinyl Terminated Diphenylsiloxane-Dimethylsiloxane Copolymers) FMV (Vinyl Terminated TrifluoropropylMethylsiloxane-Dimethylsiloxane Copolymer), CMS ((Carbinol functional)Methyl siloxane-Dimethylsiloxane Copolymers).

In some embodiments, the oligomeric or polymeric additive can include a fluorocarbon monomer. The fluorocarbon monomer may be represented by the following formula:

D-E-F wherein D is a polymerizable group selected from acrylate, methacrylate or vinyl or an active hydrogen group selected from an alcohol, an amine or a thiol, E is an optional linking group; and F is fluorocarbon group which can be perfluorinated or partially fluorinated.

Suitable fluorocarbon monomers include, but are not limited to 1,1,1,3,3,3-hexafluoroisopropyl acrylate, 1,1,1,3, 3,3-hexafluoroisopropyl methacrylate, 2,2,3,4,4,4-hexafluorobutyl methacrylate, 2,2,3,3-tetrafluoropropyl methacrylate, 2,2,2-trifluoroethyl methacrylate, 2,2,3,3,4,4,4-heptafluorobutyl acrylate, 2,2,3,3,4,4,4-Heptafluorobutyl methacrylate, 2,2,3,3,3-Pentafluoropropyl acrylate, 2,2,3,3,4,4,5,5-Octafluoropentyl methacrylate, 2,2,3,3,3-Pentafluoropropyl methacrylate, 3,3,4,4,5,5,6,6,7,7,8,8,8-Tridecafluorooctyl methacrylate, 3,3,4,4,5,5,6,6,7,7,8,8,9,9,10,10,10-Heptadecafluorodecyl methacrylate, 3,3,4,4,5,5,6,6,7,7,8,8,8-Tridecafluorooctyl acrylate, 3,3,4,4,5,5,6,6,7,7,8,8,9,9,10,10,11,11,12,12,12-Heneicosafluorododecyl acrylate, 2,2,3,3,4,4,5,5-Octafluoropentyl acrylate, 2,2,3,3,4,4,5,5,6,6,7,7-Dodecafluoroheptyl acrylate 95%, 2,2,3,4,4,4-Hexafluorobutyl acrylate, 1H,1H,2H,2H-Perfluorodecyl acrylate, 2-[(1',1',1'-Trifluoro-2'-(trifluoromethyl)-2'-hydroxy)propyl]-3-norbornyl methacrylate, 1,1,1-Trifluoro-2-(trifluoromethyl)-2-hydroxy-4-methyl-5-pentyl methacrylate, 2-(Perfluorohexyl)ethyl methacrylate, Perfluorohexylethyl alcohol, 4-Vinylbenzyl Hexafluoroisopropyl Ether, 4-Vinylbenzyl Perfluorooctanoate, 4-Vinylbenzyl Trifluoroacetate, Allyl Heptafluorobutyrate, Allyl Perfluoroheptanoate, Allyl Perfluorononanoate, Allyl Perfluorooctanoate, Allyl Tetrafluoroethyl Ether, Allyl Trifluoroacetate, and Allylpentafluorobenzene The silicone or fluorocarbon monomer can be present, in one embodiment, in an amount from about 5% to about 40% of the total monomer composition of the additive.

The Alkyl Substituted Monomer

In some embodiments, the oligomeric or polymeric additive includes an adhesion-promoting monomer. The adhesion-promoting monomer can include an alkyl substituted monomer. In one embodiment, the alkyl substituted monomer includes a methacrylate, an acrylate, an acrylamide or a vinyl monomer, or combinations thereof. Suitable monomers include, but are not limited to, substituted acrylates and methacrylates such as methyl methacrylate, ethyl acrylate, butyl acrylate, butyl methacrylate, 2-ethylhexylmethacrylate, mono and other similar monomers which will be readily obvious to those skilled in the art. The monomer may be chosen such that, when included in the additive, it will increase the affinity of the additive to the base polymer. In some embodiments, the alkyl substituted monomer will be present in the additive in an amount of from about 10 mole % to about 70 mole % of the total monomer composition of the additive.

In some embodiments, the alkyl substituted monomer can include hydroxyalkyl acrylates, acrylates with primary, secondary, or tertiary amino groups, and reactive or crosslinkable acrylate, such as acrylates containing silyl groups, double bonds, or other reactive functional groups; acrylamides, including substituted acrylamides as described above for acrylates; vinyl compounds; multifunctional molecules, such as di-, tri-, and tetraisocyanates, di-, tri-, and tetraols, di-, tri-, and tetraamines, and di-, tri-, and tetrathiocyanates; cyclic monomers, such as lactones and lactams; and combinations thereof; Alkyl methacrylates or other hydrophobic methacrylates, such as ethyl methacrylate, butyl methacrylate, hexyl methacrylate, 2-ethylhexyl methacrylate, methyl methacrylate, lauryl methacrylate, isobutyl methacrylate, isodecyl methacrylate, phenyl methacrylate, decyl methacrylate, 3,3,5-trimethylcyclohexyl methacrylate, benzyl methacrylate, cyclohexyl methacrylate, stearyl methacrylate, tert-butyl methacrylate, tridecyl methacrylate, and 2-naphthyl methacrylate; Reactive or crosslinkable methacrylates, such as 2-(trimethylsilyloxy)-ethylmethacrylate, 3-(trichlorosilyl)propyl methacrylate, 3-(trimethoxysilyl)propyl methacrylate, 3-[tris(trimethylsiloxy)silyl]propyl methacrylate, trimethylsilyl methacrylate, allyl methacrylate, vinyl methacrylate, 3-(acryloyloxy)-2-hydroxypropyl methacrylate, 3-(diethoxymethylsilyl)propyl methacrylate, 3-(dimethylchlorosilyl)propyl methacrylate, isocyanates, such as 2-isocyanatoethyl methacrylate, glycidyl methacrylate, 2-hydroxyethyl methacrylate, 3-chloro-2-hydroxypropyl methacrylate, Hydroxybutyl methacrylate, glycol methacrylate, hydroxypropyl methacrylate, and 2-hydroxypropyl 2-(methacryloyloxy)ethyl phthalate.

The amount of the various monomers used to make the additives of the invention are typically in the range of 10-60 mole percent of the total additive composition. The amount of each particular monomer which is useful in the invention will depend on which specific monomer from each class of monomers is used and the base polymer into which the additive is being blended. For example, for a PTMEG based aromatic TPU, additives which contain from about 10 to about 30 mole percent of a fluorocarbon methacrylates, from about 10 to about 30 percent of polyethyleneglycol methacrylate and from about 40 to about 80 percent of methylmethacrylate has been shown to be effective to impart non-fouling and/or non-thrombogenic surfaces to the TPU base polymer with which it is blended.

Synthesis of Oligomeric or Polymeric Additives

The oligomeric or polymeric additive as disclosed herein may be formed via addition polymerization (radical, cationic and ionic) or condensation polymerization. In one embodiment, the additive is formed using addition polymerization, in which, for example, mixed monomer solution and radical initiator are metered into a reactor to allow the reaction for approximately over 4 hours and allowed to post-react for an additional 14 hours. The reaction temperature and time will be dependent on the initiator used. For example, for AIBN the reaction temperatyure is 70 C and the time are as given above. The additives are then recovered by stripping off solvent.

In one embodiment, the additive is formed using condensation polymerization, in which, for example, a diisocyanate is allowed to react with Tegomer® (a diol monomer available from Evonik with a pendant PEG group) to form a prepolymer with free terminal isocyanate groups. Monofunctional fluorinated or polysiloxanes such as Capstone® 62AL (available from DuPont) react with prepolymers to end-cap the prepolymer to form oligomeric/polymeric additives with urethane and/or urea bonds.

The Base Polymer

The surface modified polymer compositions described herein include a base polymer. In some embodiments, the base polymer includes a thermoplastic polyurethane, a nylon, a polyethylene, a polyester, a polyvinylchloride, a polysulfone, a polysiloxane, a polyether sulfone, a polyether ether ketone (PEEK), a polycaprolactone, a polydioxanone, a poly(1,3-trimethylene carbonate), a polytyrosine carbonate, a polyacrylate, a polymethacrylate, polylactic acid, polyglycolic acid, a polypropylene, a polycarbonate, and combinations thereof.

In one embodiment, the base polymer is a thermoplastic polyurethane. The TPU compositions described herein are made using: (a) a polyisocyanate. (b) a polyol; and optionally (a chain extender). The TPU may be present in the surface modified polymer in an amount from about_80_to about 99.9 wt percent.

The Polyisocyanate

The TPU compositions described herein are made using a) a polyisocyanate component. The polyisocyanate and/or polyisocyanate component includes one or more polyisocyanates. In some embodiments, the polyisocyanate component includes one or more diisocyanates.

In some embodiments, the polyisocyanate and/or polyisocyanate component includes an α,ω-alkylene diisocyanate having from 5 to 20 carbon atoms.

Suitable polyisocyanates include aromatic diisocyanates, aliphatic diisocyanates, or combinations thereof. In some embodiments, the polyisocyanate component includes one or more aromatic diisocyanates. In some embodiments, the polyisocyanate component is essentially free of, or even completely free of, aliphatic diisocyanates. In other embodiments, the polyisocyanate component includes one or more aliphatic diisocyanates. In some embodiments, the polyisocyanate component is essentially free of, or even completely free of, aromatic diisocyanates.

Examples of useful polyisocyanates include aromatic diisocyanates such as 4,4'-methylenebis(phenyl isocyanate) (MDI), m-xylene diisocyanate (XDI), phenylene-1,4-diisocyanate, naphthalene-1,5-diisocyanate, and toluene diisocyanate (TDI); as well as aliphatic diisocyanates such as isophorone diisocyanate (IPDI), 1,4-cyclohexyl diisocyanate (CHDI), decane-1,10-diisocyanate, lysine diisocyanate (LDI), 1,4-butane diisocyanate (BDI), isophorone diisocyanate (PDI), 3,3'-dimethyl-4,4'-biphenylene diisocyanate (TODI), 1,5-naphthalene diisocyanate (NDI), and dicyclohexylmethane-4,4'-diisocyanate (H12MDI). Mixtures of two or more polyisocyanates may be used. In some embodiments, the polyisocyanate is MDI and/or H12MDI. In some embodiments, the polyisocyanate includes MDI. In some embodiments, the polyisocyanate includes H12MDI.

In some embodiments, the thermoplastic polyurethane is prepared with a polyisocyanate component that includes H12MDI. In some embodiments, the thermoplastic polyurethane is prepared with a polyisocyanate component that consists essentially of H12MDI. In some embodiments, the thermoplastic polyurethane is prepared with a polyisocyanate component that consists of H12MDI.

In some embodiments, the thermoplastic polyurethane is prepared with a polyisocyanate component that includes (or consists essentially of, or even consists of) H12MDI and at least one of MDI, HDI, TDI, IPDI, LDI, BDI, PDI, CHDI, TODI, and NDI.

In some embodiments, the polyisocyanate used to prepare the TPU and/or TPU compositions described herein is at least 50%, on a weight basis, a cycloaliphatic diisocyanate. In some embodiments, the polyisocyanate includes an α,ω-alkylene diisocyanate having from 5 to 20 carbon atoms.

In some embodiments, the polyisocyanate used to prepare the TPU and/or TPU compositions described herein includes hexamethylene-1,6-diisocyanate, 1,12-dodecane diisocyanate, 2,2,4-trimethyl-hexamethylene diisocyanate, 2,4,4-trimethyl-hexamethylene diisocyanate, 2-methyl-1,5-pentamethylene diisocyanate, or combinations thereof.

The Polyol Component

The TPU compositions described herein are made using: (b) a polyol component.

Polyols include polyether polyols, polyester polyols, polycarbonate polyols, polysiloxane polyols, and combinations thereof.

Suitable polyols, which may also be described as hydroxyl terminated intermediates, when present, may include one or more hydroxyl terminated polyesters, one or more hydroxyl terminated polyethers, one or more hydroxyl terminated polycarbonates, one or more hydroxyl terminated polysiloxanes, or mixtures thereof.

Suitable hydroxyl terminated polyester intermediates include linear polyesters having a number average molecular weight (Mn) of from about 500 to about 10,000, from about 700 to about 5,000, or from about 700 to about 4,000, and generally have an acid number less than 1.3 or less than 0.5. The molecular weight is determined by assay of the terminal functional groups and is related to the number average molecular weight. The polyester intermediates may be produced by (1) an esterification reaction of one or more glycols with one or more dicarboxylic acids or anhydrides or (2) by transesterification reaction, i.e., the reaction of one or more glycols with esters of dicarboxylic acids. Mole ratios generally in excess of more than one mole of glycol to acid are preferred so as to obtain linear chains having a preponderance of terminal hydroxyl groups. Suitable polyester intermediates also include various lactones such as polycaprolactone typically made from ε-caprolactone and a bifunctional initiator such as diethylene glycol. The dicarboxylic acids of the desired polyester can be aliphatic, cycloaliphatic, aromatic, or combinations thereof. Suitable dicarboxylic acids which may be used alone or in mixtures generally have a total of from 4 to 15 carbon atoms and include: succinic, glutaric, adipic, pimelic, suberic, azelaic, sebacic, dodecanedioic, isophthalic, terephthalic, cyclohexane dicarboxylic, and the like. Anhydrides of the above dicarboxylic acids such as phthalic anhydride, tetrahydrophthalic anhydride, or the like, can also be used. Adipic acid is a preferred acid. The glycols which are reacted to form a desirable polyester intermediate can be aliphatic, aromatic, or combinations thereof, including any of the glycols described above in the chain extender section, and have a total of from 2 to 20 or from 2 to 12 carbon atoms. Suitable examples include ethylene glycol, 1,2-propanediol, 1,3-propanediol, 1,3-butanediol, 1,4-butanediol, 1,5-pentanediol, 1,6-hexanediol, 2,2-dimethyl-1,3-propanediol, 1,4-cyclohexanedimethanol, decamethylene glycol, dodecamethylene glycol, and mixtures thereof.

The polyol component may also include one or more polycaprolactone polyester polyols. The polycaprolactone polyester polyols useful in the technology described herein include polyester diols derived from caprolactone monomers. The polycaprolactone polyester polyols are terminated by primary hydroxyl groups. Suitable polycaprolactone polyester polyols may be made from ε-caprolactone and a bifunctional initiator such as diethylene glycol, 1,4-butanediol, or any of the other glycols and/or diols listed herein. In some embodiments, the polycaprolactone polyester polyols are linear polyester diols derived from caprolactone monomers.

Useful examples include CAPA™ 2202A, a 2,000 number average molecular weight (Mn) linear polyester diol, and CAPA™ 2302A, a 3,000 Mn linear polyester diol, both of which are commercially available from Perstorp Polyols Inc. These materials may also be described as polymers of 2-oxepanone and 1,4-butanediol.

The polycaprolactone polyester polyols may be prepared from 2-oxepanone and a diol, where the diol may be 1,4-butanediol, diethylene glycol, monoethylene glycol, 1,6-hexanediol, 2,2-dimethyl-1,3-propanediol, or any combination thereof. In some embodiments, the diol used to prepare the polycaprolactone polyester polyol is linear. In some embodiments, the polycaprolactone polyester polyol is prepared from 1,4-butanediol. In some embodiments, the polycaprolactone polyester polyol has a number average molecular weight from 500 to 10,000, or from 500 to 5,000, or from 1,000 or even 2,000 to 4,000 or even 3,000.

Suitable hydroxyl terminated polyether intermediates include polyether polyols derived from a diol or polyol having a total of from 2 to 15 carbon atoms, in some embodiments an alkyl diol or glycol which is reacted with an ether comprising an alkylene oxide having from 2 to 6 carbon atoms, typically ethylene oxide or propylene oxide or mixtures thereof. For example, hydroxyl functional polyether can be produced by first reacting propylene glycol with propylene oxide followed by subsequent reaction with ethylene oxide. Primary hydroxyl groups resulting from ethylene oxide are more reactive than secondary hydroxyl groups and thus are preferred. Useful commercial polyether polyols include poly(ethylene glycol) comprising ethylene oxide reacted with ethylene glycol, poly(propylene glycol) comprising propylene oxide reacted with propylene glycol, poly(tetramethylene ether glycol) comprising water reacted with tetrahydrofuran which can also be described as polymerized tetrahydrofuran, and which is commonly referred to as PTMEG. In some embodiments, the polyether intermediate includes PTMEG. Suitable polyether polyols also include polyamide adducts of an alkylene oxide and can include, for example, ethylenediamine adduct comprising the reaction product of ethylenediamine and propylene oxide, diethylenetriamine adduct comprising the reaction product of diethylenetriamine with propylene oxide, and similar polyamide type polyether polyols. Copolyethers can also be utilized in the described compositions. Typical copolyethers include the reaction product of THF and ethylene oxide or THF and propylene oxide. These are available from BASF as PolyTHF® B, a block copolymer, and PolyTHF® R, a random copolymer. The various polyether intermediates generally have a number average molecular weight (Mn) as determined by assay of the terminal functional groups which is an average molecular weight greater than about 700, such as from about 700 to about 10,000, from about 1,000 to about 5,000, or from about 1,000 to about 2,500. In some embodiments, the polyether intermediate includes a blend of two or more different molecular weight polyethers, such as a blend of 2,000 Mn and 1,000 Mn PTMEG.

Suitable hydroxyl terminated polycarbonates include those prepared by reacting a glycol with a carbonate. U.S. Pat. No. 4,131,731 is hereby incorporated by reference for its disclosure of hydroxyl terminated polycarbonates and their preparation. Such polycarbonates are linear and have terminal hydroxyl groups with essential exclusion of other terminal groups. The essential reactants are glycols and carbonates. Suitable glycols are selected from cycloaliphatic and aliphatic diols containing 4 to 40, and or even 4 to 12 carbon atoms, and from polyoxyalkylene glycols containing 2 to 20 alkoxy groups per molecule with each alkoxy group containing 2 to 4 carbon atoms. Suitable diols include aliphatic diols containing 4 to 12 carbon atoms such as 1,4-butanediol, 1,5-pentanediol, neopentyl glycol, 1,6-hexanediol, 2,2,4-trimethyl-1,6-hexanediol, 1,10-decanediol, hydrogenated dilinoleylglycol, hydrogenated dioleylglycol, 3-methyl-1,5-pentanediol; and cycloaliphatic diols such as 1,3-cyclohexanediol, 1,4-dimethylolcyclohexane, 1,4-cyclohexanediol-, 1,3-dimethylolcyclohexane-, 1,4-endomethylene-2-hydroxy-5-hydroxymethyl cyclohexane, and polyalkylene glycols. The diols used in the reaction may be a single diol or a mixture of diols depending on the properties desired in the finished product. Polycarbonate intermediates which are hydroxyl terminated are generally those known to the art and in the literature. Suitable carbonates are selected from alkylene carbonates composed of a 5 to 7 member ring. Suitable carbonates for use herein include ethylene carbonate, trimethylene carbonate, tetramethylene carbonate, 1,2-propylene carbonate, 1,2-butylene carbonate, 2,3-butylene carbonate, 1,2-ethylene carbonate, 1,3-pentylene carbonate, 1,4-pentylene carbonate, 2,3-pentylene carbonate, and 2,4-pentylene carbonate. Also, suitable herein are dialkylcarbonates, cycloaliphatic carbonates, and diarylcarbonates. The dialkylcarbonates can contain 2 to 5 carbon atoms in each alkyl group and specific examples thereof are diethylcarbonate and dipropylcarbonate. Cycloaliphatic carbonates, especially dicycloaliphatic carbonates, can contain 4 to 7 carbon atoms in each cyclic structure, and there can be one or two of such structures. When one group is cycloaliphatic, the other can be either alkyl or aryl. On the other hand, if one group is aryl, the other can be alkyl or cycloaliphatic. Examples of suitable diarylcarbonates, which can contain 6 to 20 carbon atoms in each aryl group, are diphenyl carbonate, ditolylcarbonate, and dinaphthylcarbonate.

Suitable polysiloxane polyols include α-ω-hydroxyl or amine or carboxylic acid or thiol or epoxy terminated polysiloxanes. Examples include poly(dimethysiloxane) terminated with a hydroxyl or amine or carboxylic acid or thiol or epoxy group. In some embodiments, the polysiloxane polyols are hydroxyl terminated polysiloxanes. In some embodiments, the polysiloxane polyols have a number-average molecular weight in the range from 300 to 5,000, or from 400 to 3,000.

Polysiloxane polyols may be obtained by the dehydrogenation reaction between a polysiloxane hydride and an aliphatic polyhydric alcohol or polyoxyalkylene alcohol to introduce the alcoholic hydroxy groups onto the polysiloxane backbone.

In some embodiments, the polysiloxane polyols may be represented by one or more compounds having the following formula:

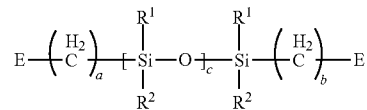

in which: each R1 and R2 are independently a 1 to 4 carbon atom alkyl group, a benzyl, or a phenyl group; each E is OH or $NHR^3$ where $R^3$ is hydrogen, a 1 to 6 carbon atoms alkyl group, or a 5 to 8 carbon atoms cyclo-alkyl group; a and b are each independently an integer from 2 to 8; c is an integer from 3 to 50. In amino-containing polysiloxanes, at least one of the E groups is $NHR^3$. In the hydroxyl-containing polysiloxanes, at least one of the E groups is OH. In some embodiments, both $R^1$ and $R^2$ are methyl groups.

Suitable examples include α,ω-hydroxypropyl terminated poly(dimethysiloxane) and α,ω-amino propyl terminated poly(dimethysiloxane), both of which are commercially available materials. Further examples include copolymers of the poly(dimethysiloxane) materials with a poly(alkylene oxide).

The polyol component, when present, may include poly(ethylene glycol), poly(tetramethylene ether glycol), poly(trimethylene oxide), ethylene oxide capped poly(propylene glycol), poly(butylene adipate), poly(ethylene adipate), poly(hexamethylene adipate), poly(tetramethylene-co-hexamethylene adipate), poly(3-methyl-1,5-pentamethylene adipate), polycaprolactone diol, poly(hexamethylene carbonate) glycol, poly(pentamethylene carbonate) glycol, poly(trimethylene carbonate) glycol, dimer fatty acid based polyester polyols, vegetable oil based polyols, or any combination thereof.

Examples of dimer fatty acids that may be used to prepare suitable polyester polyols include Priplast™ polyester glycols/polyols commercially available from Croda and Radia® polyester glycols commercially available from Oleon.

In some embodiments, the polyol component includes a polyether polyol, a polycarbonate polyol, a polycaprolactone polyol, or any combination thereof.

In some embodiments, the polyol component includes a polyether polyol. In some embodiments, the polyol component is essentially free of or even completely free of polyester polyols. In some embodiments, the polyol component used to prepare the TPU is substantially free of, or even completely free of polysiloxanes.

In some embodiments, the polyol component includes ethylene oxide, propylene oxide, butylene oxide, styrene oxide, poly(tetramethylene ether glycol), poly(propylene glycol), poly(ethylene glycol), copolymers of poly(ethylene glycol) and poly(propylene glycol), epichlorohydrin, and the like, or combinations thereof. In some embodiments the polyol component includes poly(tetramethylene ether glycol).

The Chain Extender

The TPU compositions described herein are made using c) a chain extender component. Chain extenders include diols, diamines, and combination thereof.

Suitable chain extenders include relatively small polyhydroxy compounds, for example lower aliphatic or short chain glycols having from 2 to 20, or 2 to 12, or 2 to 10 carbon atoms. Suitable examples include ethylene glycol, diethylene glycol, propylene glycol, dipropylene glycol, 1,4-butanediol (BDO), 1,6-hexanediol (HDO), 1,3-butanediol, 1,5-pentanediol, neopentylglycol, 1,4-cyclohexanedimethanol (CHDM), 2,2-bis[4-(2-hydroxyethoxy)phenyl]propane (HEPP), hexamethylenediol, heptanediol, nonanediol, dodecanediol, 3-methyl-1,5-pentanediol, ethylenediamine, butanediamine, hexamethylenediamine, and hydroxyethyl resorcinol (HER), and the like, as well as mixtures thereof. In some embodiments the chain extender includes BDO, HDO, 3-methyl-1,5-pentanediol, or a combination thereof. In some embodiments, the chain extender includes BDO. Other glycols, such as aromatic glycols could be used, but in some embodiments the TPUs described herein are essentially free of or even completely free of such materials.

In some embodiments, the chain extender used to prepare the TPU is substantially free of, or even completely free of, 1,6-hexanediol. In some embodiments, the chain extender used to prepare the TPU includes a cyclic chain extender. Suitable examples include CHDM, HEPP, HER, and combinations thereof. In some embodiments, the chain extender used to prepare the TPU includes an aromatic cyclic chain extender, for example HEPP, HER, or a combination thereof. In some embodiments, the chain extender used to prepare the TPU includes an aliphatic cyclic chain extender, for example CHDM. In some embodiments, the chain extender used to prepare the TPU is substantially free of, or even completely free of aromatic chain extenders, for example aromatic cyclic chain extenders. In some embodiments, the chain extender used to prepare the TPU is substantially free of, or even completely free of polysiloxanes.

In some embodiments, the chain extender component includes 1,4-butanediol, 2-ethyl-1,3-hexanediol, 2,2,4-trimethyl pentane-1,3-diol, 1,6-hexanediol, 1,4-cyclohexane dimethylol, 1,3-propanediol, 3-methyl-1,5-pentanediol or combinations thereof. In some embodiments, the chain extender component includes 1,4-butanediol, 3-methyl-1,5-pentanediol or combinations thereof. In some embodiments, the chain extender component includes 1,4-butanediol.

The described compositions include the TPU materials described above and also TPU compositions that include such TPU materials and one or more additional components. These additional components include other polymeric materials that may be blended with the TPU described herein. These additional components also include one or more additives that may be added to the TPU, or blend containing the TPU, to impact the properties of the composition.

The TPU described herein may also be blended with one or more other polymers. The polymers with which the TPU described herein may be blended are not overly limited. In some embodiments, the described compositions include two or more of the described TPU materials. In some embodiments, the compositions include at least one of the described TPU materials and at least one other polymer, which is not one of the described TPU materials. In some embodiments, the described blends will have the same combination of properties described above for the TPU composition. In other embodiments, the TPU composition will of course have the described combination of properties, while the blend of the TPU composition with one or more of the other polymeric materials described above may or may not.

Polymers that may be used in combination with the TPU materials described herein also include more conventional TPU materials such as non-caprolactone polyester-based TPU, polyether-based TPU, or TPU containing both non-caprolactone polyester and polyether groups. Other suitable materials that may be blended with the TPU materials described herein include polycarbonates, polyolefins, styrenic polymers, acrylic polymers, polyoxymethylene polymers, polyamides, polyphenylene oxides, polyphenylene sulfides, polyvinylchlorides, chlorinated polyvinyl chlorides, polylactic acids, or combinations thereof.

Polymers for use in the blends described herein include homopolymers and copolymers. Suitable examples include: (i) a polyolefin (PO), such as polyethylene (PE), polypropylene (PP), polybutene, ethylene propylene rubber (EPR), polyoxyethylene (POE), cyclic olefin copolymer (COC), or combinations thereof; (ii) a styrenic, such as polystyrene (PS), acrylonitrile butadiene styrene (ABS), styrene acrylonitrile (SAN), styrene butadiene rubber (SBR or HIPS), polyalphamethylstyrene, styrene maleic anhydride (SMA), styrene-butadiene copolymer (SBC) (such as styrene-butadiene-styrene copolymer (SBS) and styrene-ethylene/butadiene-styrene copolymer (SEBS)), styrene-ethylene/propylene-styrene copolymer (SEPS), styrene butadiene latex (SBL), SAN modified with ethylene propylene diene monomer (EPDM) and/or acrylic elastomers (for example, PS-SBR copolymers), or combinations thereof; (iii) a thermoplastic polyurethane (TPU) other than those described above; (iv) a polyamide, such as Nylon™, including polyamide 6,6 (PA66), polyamide 1,1 (PA11), polyamide 1,2 (PA12), a copolyamide (COPA), or combinations thereof; (v) an acrylic polymer, such as polymethyl acrylate, polymethylmethacrylate, a methyl methacrylate styrene (MS) copolymer, or combinations thereof; (vi) a polyvinylchloride (PVC), a chlorinated polyvinylchloride (CPVC), or combinations thereof; (vii) a polyoxyemethylene, such as polyacetal; (viii) a polyester, such as polyethylene terephthalate (PET), polybutylene terephthalate (PBT), copolyesters and/or polyester elastomers (COPE) including polyetherester block copolymers such as glycol modified polyethylene terephthalate (PETG), polylactic acid (PLA), polyglycolic acid (PGA), copolymers of PLA and PGA, or combinations thereof; (ix) a polycarbonate (PC), a polyphenylene sulfide (PPS), a polyphenylene oxide (PPO), or combinations thereof; or combinations thereof.

In some embodiments, these blends include one or more additional polymeric materials selected from groups (i), (iii), (vii), (viii), or some combination thereof. In some embodiments, these blends include one or more additional polymeric materials selected from group (i). In some embodiments, these blends include one or more additional polymeric materials selected from group (iii). In some embodiments, these blends include one or more additional polymeric materials selected from group (vii). In some embodiments, these blends include one or more additional polymeric materials selected from group (viii).

The additional additives suitable for use in the TPU compositions described herein are not overly limited. Suitable additives include pigments, UV stabilizers, UV absorbers, antioxidants, lubricity agents, heat stabilizers, hydrolysis stabilizers, cross-linking activators, flame retardants, layered silicates, fillers, colorants, reinforcing agents, adhesion mediators, impact strength modifiers, antimicrobials, radio-paque additives, for example, barium sulfate, bismuth subcarbonate, bismuth trioxide, bismuth oxychloride, tantalum, and tungsten, amongst others, and any combination thereof.

In some embodiments, the additional component is a flame retardant. Suitable flame retardants are not overly limited and may include a boron phosphate flame retardant, a magnesium oxide, a dipentaerythritol, a polytetrafluoroethylene (PTFE) polymer, or any combination thereof. In some embodiments, this flame retardant may include a boron phosphate flame retardant, a magnesium oxide, a dipentaerythritol, or any combination thereof. A suitable example of a boron phosphate flame retardant is BUDIT®-326, commercially available from Budenheim USA, Inc. When present, the flame retardant component may be present in an amount from 0 to 10 weight percent of the overall TPU composition, in other embodiments from 0.5 to 10, or from 1 to 10, or from 0.5 or 1 to 5, or from 0.5 to 3, or even from 1 to 3 weight percent of the overall TPU composition.

The TPU compositions described herein may also include additional additives, which may be referred to as a stabilizer. The stabilizers may include antioxidants such as phenolics, phosphites, thioesters, and amines, light stabilizers such as hindered amine light stabilizers and benzothiazole UV absorbers, and other process stabilizers and combinations thereof. In one embodiment, the preferred stabilizer is Irganox®-1010 from BASF and Naugard®-445 from Chemtura. The stabilizer is used in the amount from about 0.1 weight percent to about 5 weight percent, in another embodiment from about 0.1 weight percent to about 3 weight percent, and in another embodiment from about 0.5 weight percent to about 1.5 weight percent of the TPU composition.

In addition, various conventional inorganic flame retardant components may be employed in the TPU composition. Suitable inorganic flame retardants include any of those known to one skilled in the art, such as metal oxides, metal oxide hydrates, metal carbonates, ammonium phosphate, ammonium polyphosphate, calcium carbonate, antimony oxide, clay, mineral clays including talc, kaolin, wollastonite, nanoclay, montmorillonite clay which is often referred to as nano-clay, and mixtures thereof. In one embodiment, the flame retardant package includes talc. The talc in the flame retardant package promotes properties of high limiting oxygen index (LOI). The inorganic flame retardants may be used in the amount from 0 to about 30 weight percent, from about 0.1 weight percent to about 20 weight percent, in another embodiment about 0.5 weight percent to about 15 weight percent of the total weight of the TPU composition.

Still further optional additives may be used in the TPU compositions described herein. The additives include colorants, antioxidants (including phenolics, phosphites, thioesters, and/or amines), antiozonants, stabilizers, inert fillers, lubricants, inhibitors, hydrolysis stabilizers, light stabilizers, hindered amines light stabilizers, benzotriazole UV absorber, heat stabilizers, stabilizers to prevent discoloration, dyes, pigments, inorganic and organic fillers, reinforcing agents and combinations thereof.

All of the additives described above may be used in an effective amount customary for these substances. The nonflame retardants additives may be used in amounts of from about 0 to about 30 weight percent, in one embodiment from about 0.1 to about 25 weight percent, and in another embodiment about 0.1 to about 20 weight percent of the total weight of the TPU composition.

These additional additives can be incorporated into the components of, or into the reaction mixture for, the preparation of the TPU resin, or after making the TPU resin. In another process, all the materials can be mixed with the TPU resin and then melted or they can be incorporated directly into the melt of the TPU resin.

The thermoplastic polyurethanes of the invention can be prepared by processes which are conventional in the art for the synthesis of polyurethane elastomers such as but not limited to a batch process or a one-shot technique. In the batch process, the components, i.e., the diisocyanate(s), the polyol(s), and the chain extenders(s), as well as the catalyst (s) and any other additive(s), if desired, are introduced into a container, mixed, dispensed into trays and allowed to cure. The cured TPU can then be granulated and pelletized. The one-shot procedure is performed in an extruder, e.g. single screw, twin screw, wherein the formative components, introduced individually or as a mixture into the extruder, and reacted at a temperature generally in one embodiment from about 100° C. to about 300° C., and in another embodiment from about 150° C. to about 250° C., and even from about 150° C. to about 240° C.

One or more polymerization catalysts may be present during the polymerization reaction. Generally, any conventional catalyst can be utilized to react the diisocyanate with the polyol intermediates or the chain extender. Examples of suitable catalysts which in particular accelerate the reaction between the NCO groups of the diisocyanates and the hydroxy groups of the polyols and chain extenders are the conventional tertiary amines known from the prior art, e.g. triethylamine, dimethylcyclohexylamine, N-methylmorpholine, N,N'-dimethylpiperazine, 2-(dimethylaminoethoxy) ethanol, diazabicyclo[2.2.2]octane and the like, and also in particular organometallic compounds, such as titanic esters, iron compounds, e.g. ferric acetylacetonate, tin compounds, e.g. stannous diacetate, stannous dioctoate, stannous dilaurate, or the dialkyltin salts of aliphatic carboxylic acids, e.g. dibutyltin diacetate, dibutyltin dilaurate, or the like. The amounts usually used of the catalysts are from 0.0001 to 0.1 part by weight per 100 parts by weight of polyhydroxy compound (b).

The process may further include the step of: (II) mixing the TPU composition of step (I) with one or more blend components, including one or more additional TPU materials and/or polymers, including any of those described above.

The process may further include the step of: (II) mixing the TPU composition of step (I) with one or more additional additives selected from the group consisting of pigments, UV stabilizers, UV absorbers, antioxidants, lubricity agents, heat stabilizers, hydrolysis stabilizers, cross-linking activators, flame retardants, layered silicates, fillers, colorants, reinforcing agents, adhesion mediators, impact strength modifiers, and antimicrobials.

The process may further include the step of: (II) mixing the TPU composition of step (I) with one or more blend components, including one or more additional TPU materials and/or polymers, including any of those described above, and/or the step of: (III) mixing the TPU composition of step (I) with one or more additional additives selected from the group consisting of pigments, UV stabilizers, UV absorbers, antioxidants, lubricity agents, heat stabilizers, hydrolysis stabilizers, cross-linking activators, flame retardants, layered silicates, fillers, colorants, reinforcing agents, adhesion mediators, impact strength modifiers, and antimicrobials.

The Surface-Modified Polymer Compositions

The surface-modified polymer compositions may be prepared by melt processing of the additive into the polymer, incorporation of the additive during polymer synthesis, casting, spinning, precipitating or coagulating a solvent mixture containing the additive and the polymer, or coating of the polymer composition onto a material.

In some embodiments, where the base polymer is a TPU, the diisocyanate, polyols and chain extender are mixed together either with or without catalysts, depending on the type of TPU being used. During the reaction, the polymeric or oligomeric surface modifying additives are preheated at 100° C. are poured into the reaction mixture. The resulting surface-modified TPU polymer can then be cut into cookies and granulated for extrusion or compression molding processes.

The surface modified polymer compositions may be prepared by melt mixing of the oligomeric or polymeric additives using a Brabender Plasticorder with the mixing bowl attachment. In some embodiments, the blends are run with the additives and the TPU are mixed as a mixture of solids (salt and pepper) prior to melt mixing. In some embodiments, the additive may be added to the base polymer following the initial charge of the base TPU had melted and the torque had stabilized. Alternatively, a twin screw extruder can be used to melt mix the additive into the TPU via typical methods know to those skilled in the art.

In one embodiment the surface-modified polymer composition may be coated onto a material. The material may include a polymer, a glass, a ceramic, a metal, or a composite. The method of application of the coating is not overly limited, and can include dip coating, spray coating, roll-to-roll coating or spin coating. The coating may be applied at a thickness of from about 1 micrometer to about 200 micrometers, or from about 5 micrometers to about 100 micrometers. The coated polymer may then be dried in an oven for approximately, 24 hrs at 80° C. In some embodiments, following coating of the base polymer, a further step of annealing may be performed, as described below.

In some embodiments, the polymer compositions may be printed on a material forming an article. The printing methods are not overly limited, and may include such methods as additive manufacturing digital printing, and the like, as well as other printing methods known to those skilled in the art.

In a further embodiment, the polymer compositions may include a further processing step in which the compositions are annealed. In one embodiment, annealing may be accomplished in an oven at temperature of from about 30 C up to about 150 C, or from about 50 C to about 80 C. In a further embodiment, annealing may be performed at a temperature of from about the glass transition temperature of the base polymer up to about the melting point of the base polymer. In some embodiments, annealing can occur for periods of from about two hours up to about seventy-two hours, or from 24 hours to 48 hours. In one embodiment, the annealing period may be for a period of at least 2 hours, or at least 12 hours, or at least 24 hours or up to 7 days.

The polymer materials and/or compositions described herein may be used in the preparation of one or more articles. The specific type of articles that may be made from the polymer materials and/or compositions described herein are not overly limited. In general, the polymer materials and/or compositions described herein may be used in any application where a non-fouling or non-thrombogenic surface is desired.

The invention further provides an article made with the surface-modified polymer materials and/or compositions described herein. In some embodiments, the article may include a medical device. Examples include but are not limited to medical applications, for example, where the polymer described herein may be used in angiography catheters, angioplasty catheters, dialysis catheters, Swan-Ganz catheters, central venous catheters, peripherally inserted central catheters and urology catheters; catheter connectors; dialysis membranes; medical tubing; wound care articles, including wound closures, staples, sutures, meshes, buttressing devices, suture reinforcements, wound care dressings, and the like; neural implants, including drains, shunts, and the like; implants, including dental implants, ocular implants, cochlear implants, breast implants, and the like; a heart valve, a heart by-pass machine, an extracorporeal device, a nerve conduit, a vascular graft, a stent, a contact lens, and the like, as well as used in, personal care applications, pharmaceutical applications, health care product applications, marine applications, or any other number of applications. In some embodiments, these articles are prepared by extruding, injection molding, or any combination thereof.

The surface modified polymer compositions as described herein can provide non-fouling and/or non-thrombogenic properties to the article prepared with the composition. In some embodiments, the polymer composition provides a reduction in protein absorption of at least 50 percent, or at least 60 percent, or 70 percent.

The amount of each chemical component described is presented exclusive of any solvent which may be customarily present in the commercial material, that is, on an active chemical basis, unless otherwise indicated. However, unless otherwise indicated, each chemical or composition referred to herein should be interpreted as being a commercial grade material which may contain the isomers, by-products, derivatives, and other such materials which are normally understood to be present in the commercial grade.

It is known that some of the materials described above may interact in the final formulation, so that the components of the final formulation may be different from those that are initially added. For instance, metal ions (of, e.g., a flame retardant) can migrate to other acidic or anionic sites of other molecules. The products formed thereby, including the products formed upon employing the composition of the technology described herein in its intended use, may not be susceptible of easy description. Nevertheless, all such modifications and reaction products are included within the scope of the technology described herein; the technology described herein encompasses the composition prepared by admixing the components described above.

EXAMPLES

The technology described herein may be better understood with reference to the following non-limiting examples.

Materials

The materials are generally commercially available from chemical supply houses known to those skilled in the chemical arts or from the supplier indicated below.

| Name | Identity | Commercial source |
|---|---|---|
| Capstone MA | 2-Methyl-2-propenoic acid, 3,3,4,4,5,5,6,6,7,7,8,8,8-tridecafluorooctyl ester | DuPont |
| Capstone AL | 3,3,4,4,5,5,6,6,7,7,8,8,8-Tridecafluoro-1-octanol | DuPont |
| Trifluoroethyl MA | Trifluoroethyl methacrylate | Tosoh |
| N-i-Butyl AAM | N-iso-Butyl methyacrylamide | Sigma Aldrich |
| TPU1 | Aliphatic polyether-based TPU | Lubrizol |
| TPU2 | Aliphatic polycarbonated-based TPU | Lubrizol |
| TPU3 | Aromatic polyether-based TPU | Lubrizol |
| Tegomer D3403 | Polyether-1,3-diol | Evonik |
| Rilsan PA11 | polyamide | Arkema |
| PVC | Colorite 8011G-015 | Colorite Polymers |
| Pebax | Pebax 4033 SA 01 MED | Arkema |
| Desmodur ® W | bis(4-isocyanotocyclohexyl) methane | Bayer |
| AIBN | Azo-bis-isobutyronitrile | Sigma Aldrich |
| $H_{12}$MDI | 4,4'-Methylene dicyclohexyl diisocyanate | Bayer |
| Cotin ® 430 | dioctylbis[(1-oxododecyl)oxy]-Stannanne | Vertellus |
| PEG MA | Poly(ethylene glycol) methyl ether methacrylate (M. W. approx. 500) | Sigma Aldrich |

Methacrylate Additives

A reaction kettle is charged with solvent and preheated to desired temperature of under nitrogen purge to remove any oxygen. Monomers and initiator are mixed with solvent in amounts as set forth in Table 1 and added into the reaction kettle via a syringe pump over a period of 3-4 hours. Monomer ratios and total monomer/initiator are varied to obtain additives with different compositions and molecular weights targeting approximately 2-15,000 Daltons. The reaction is kept at the reaction temperature (70° C. for AIBN initiator) for an additional 14 hours to consume most of the monomers and initiator (residual monomer is less than 1% as measured by NMR). Polymers for the PEG series are recovered by rotatory vaporization.

Tegomer Additives—Inventive Example 5 (Table 1)

Additives containing Tegomer® are prepared by typical aliphatic TPU preparation methods known to those skilled in the art. Polyols are thoroughly melted and vigorously shaken prior to blending. Blends are prepared by premixing the ingredients (polyol(s) and chain extender(s)) in an appropriately sized glass jar or by weighing the ingredients in the amounts set forth in Table 1, directly into a reactor can. If premixing is used, all of the blend ingredients are weighed into a glass jar, the lid is tightened, and the contents are vigorously shaken to homogenize the blend. The required amount of polyol blend is poured into the reactor tin can. If weighing directly into a reactor can is the preferred procedure, then all of the blend ingredients were weighed into an appropriately sized tin can (a quart size tin can for 400-gram scale reaction). The blend was placed in the 55° C. oven to equilibrate at the temperature required for the reaction. The curing pans (Teflon coated) were preheated to 125° C. The amount of aliphatic diisocyanate (Desmodur W) plus an estimated amount of drain residue was weighed into an appropriately sized can, and it was placed in the oven to equilibrate at 55° C.

As soon as the starting reaction temperature of 55° C. was reached, the cans were removed from the oven(s) and placed in the fume hood. A firmly mounted, air driven agitator was positioned approximately ¼ inch from the bottom of the can. With slow stirring to avoid splashing, the appropriate amount of diisocyanate was then rapidly poured into the reaction can containing the polyol blend. A short time was allowed for the necessary amount of diisocyanate to drain out of the can. The catalyst was added and the starting temperature was recorded. An exothermic reaction occurs and the temperature was monitored every 30 to 60 seconds. When exothermic reaction stops, Capstone 62AL was add into the prepolymers and mixed for several minutes. The mixer was stopped and the reaction product was poured into the preheated pan. The product was then placed in the oven at 125° C. for 5 hours. After polymer had cured, the covered pan was removed from the oven and placed in a fume hood to cool. Typically the additives produced by this method were waxy or brittle solids because of low molecular weight.

TABLE 1

Additive compositions

| | Monomer (mole %) | | | | |
|---|---|---|---|---|---|
| Example # | PEG MA | Capstone MA | Methyl MA | NMR ratio | Mn/PDI |
| INV EX1 | 30 | 30 | 40 | 32/30/38 | 7.7K/2.3 |
| INV EX2 | 30 | 10 | 60 | 33/12/55 | 8.1K/2.4 |
| INV EX3 | 30 | 30 | 40 | 34/33/33 | 6.9K/2.3 |
| INV EX4 | 30 | 10 | 60 | 33/12/55 | 8.1K/2.4 |

| | $H_{12}$MDI | Tegomer | Capstone AL | BDO | Mn/DPI |
|---|---|---|---|---|---|
| INV EX5 | 0.08 | 0.07 | 0.02 | 0 | 7k/1.9 |

Extrusion of Methacrylate and Tegomer Additive TPU Blends

Each of the inventive examples in Table 1 are compounded with base TPU in order to determine if the TPU/additive blends can be extruded and to demonstrate that the products of the extrusion give bloomed surfaces, resulting in non-fouling materials when extruded. The blends are prepared by addition of 300 g of additive into 6 kg of TPU during TPU synthesis, Films are then extruded according to the conditions in Table 2. As can be seen in Table 2, the materials can be readily extruded under typical extrusion conditions.

TABLE 2

Extrusion conditions

| Sample ID | TPU1 | INV EX1 + TPU1 (Film 1) | TPU2 | INV EX2 + TPU2 (Film 2) | TPU3 | INV EX3 + TPU3 (Film 3) | INV EX4 + TPU3 (Film 4) | INV EX5 + TPU1 (Film 5) |
|---|---|---|---|---|---|---|---|---|
| Zone #1 | 176 | 166 | 171 | 154 | 190 | 171 | 171 | 165 |
| Zone #2 | 180 | 170 | 174 | 160 | 195 | 176 | 182 | 175 |

TABLE 2-continued

| | | | | Extrusion conditions | | | | |
|---|---|---|---|---|---|---|---|---|
| Sample ID | TPU1 | INV EX1 + TPU1 (Film 1) | TPU2 | INV EX2 + TPU2 (Film 2) | TPU3 | INV EX3 + TPU3 (Film 3) | INV EX4 + TPU3 (Film 4) | INV EX5 + TPU1 (Film 5) |
| Zone #3 | 180 | 177 | 177 | 160 | 198 | 176 | 204 | 175 |
| Die Temp | 170 | 182 | 180 | 171 | 203 | 176 | 204 | 155 |
| Screw RPM | 35 | 50 | 10 | 30 | 10 | 20 | 30 | 40 |
| Head Pressure | 302 | 134 | 0 | 670 | 0 | 1117 | 79 | 450 |
| Torq. Amps | 1400 | 561 | 2325 | 1419 | 2325 | 1782 | 58 | 1590 |
| Width | 1"+ | 1"+ | 1"+ | 1"+ | 1"+ | 1"+ | 1"+ | 1"+ |
| Screen Pack | N/A | N/A | N/A | N/A | N/A | N/A | N/A | N/A |
| Die Type | FILM | FILM | FILM | FILM | FILM | FILM | FILM | FILM |

Determination of Blooming of Additive to the Surface by XPS Analysis

XPS analyses of films of the pure additives and blends of the additives with TPU are performed in order to determine if the additives bloom to the surface. The XPS analyses are carried out with an Ulvac-PHI 5000 VersaProbe™ I using monochromatic Al Kα X rays as the excitation source, with an analysis spot 0.3 mm in diameter. Survey spectra are obtained with a 93.9 eV pass energy. Data analysis is performed in standard fashion with Multipak™ software, using peak areas for quantification.

TABLE 3

| | Surface XPS data | | |
|---|---|---|---|
| | 100% additive C/F and C/O | 5% C/F and C/O No surface enrichment | Inventive TPU/additive blend |
| INV EX1 + TPU1 | INV EX1 1.5/3 | 86/3.6 | Film 1 1.7/3 |
| INV EX2 + TPU2 | INV EX2 1.7/3 | 82/2.6 | Film 2 2.8/2.7 |
| INV EX3 + TPU3 | INV EX3 1.6/3 | 96/4.2 | Film 3 1.7/3 |
| INV EX4 + TPU4 | INV EX4 1.7/3 | 143/4.2 | Film 4 2.2/2.7 |
| INV EX5 + TPU5 | INV EX5 1.9/2.7 | 455/35 | Film 5 3.8/2.6 |

Table 3 illustrates the effectiveness of blooming of the additives in an extruded TPU. Blooming effectiveness is evaluated by comparing C/F (carbon/fluorine) and C/O (carbon/oxygen) ratios of 100% pure additive with an extruded film prepared from a blend of TPU and additive. Effective blooming is indicated by a similarity between the C/F and C/O ratios of the 100% pure additive and the additive/TPU blend. If no blooming is present, the C/F and C/O ratios of the extruded film will be similar to the C/F and C/O ratios of a homogenous mixture of the additive and TPU (see Column 2, Table 3). As can be seen in Table 3, the inventive surface modified TPU compositions containing the additive exhibit C/F and C/O ratios similar to the pure additive, thus indicating effective blooming.

Protein Fouling Test (Fluorescence Method)

A static test method for measuring protein adsorption on the surface of thermal processed TPUs. The method utilizes fluorescently labeled proteins to quantify the amount of protein adsorbed onto the surface of the TPU samples. The technique is similar to that as described by Hlady, et al, in *Methods for studying protein Absorption*, p. 402-429, 1999, Academic Press and Ishihara, *Why do Phospholipid Polymers Reduce Protein Absorption*, Journal of Biomedical Materials Research, p. 323-330, 1998. b. Samples of the Films from Table 2 are cut into (2.5 cm×0.6 cm coupons and the coupons are washed by shaking in 1% sodium dodecyl sulfate (SDS) and then rinsed well with deionized water and 1× phosphate buffered saline (PBS). Each washed coupon is then placed into an amber 2 ml centrifuge tube containing either fluorescently labeled fibrinogen (Fbg) or bovine serum albumin (BSA) (Alexa Fluor 488 or Alexa Fluor 594 respectively, Molecular Probes, Eugene, Oreg.). The samples are incubated at 37° C. for 1 hr, after which the coupons are removed and washed with ~25 ml 1×PBS 3 times. Using a biopsy punch, a 4.0 mm punch of each coupon is collected and placed into an 2 ml amber tube containing 1.5 ml 1% SDS. The punches are vortex cleaned and allowed to soak until analysis. The SDS solutions are transferred to cuvettes and read directly on the fluorimeter. The amount of protein adsorbed onto the TPU surface (ng/cm$^2$) is calculated by correlating fluorescence response of the labeled protein to a standard curve and dividing by the surface area of the 4 mm punch.

The results of the fluorescent protein fouling test on the Films are shown in Table 4. It can be seen that the amount of protein adsorbed onto the surface of the Films containing the inventive additives is significantly reduced compared to a base TPU with no inventive additive. In some cases, the protein adsorption is below the detection limit of the method. The actual adsorption of the proteins is in the range that has been shown to be useful in non-thrombogenic, biocompatible medical devices.

TABLE 4

BSA and Fibrinogen absorption data from fluorescence method

| | Protein fouling test (Fluorescence method) | | | |
|---|---|---|---|---|
| | BSA Binding | | Fbg Binding | |
| Sample | ng/cm$^2$ | % Decrease | ng/cm$^2$ | % Decrease |
| TPU3 | 126 | | 263 | |
| Film 3 | 3.97 | 96.8% | 14.4 | 94.5% |
| Film 4 | 1.59 | 98.7% | 4.15 | 98.4% |
| TPU1 | 166 | | 371 | |
| Film 5 | 5.05 | 97.0% | 51.7 | 86.1% |
| Film 1 | 15.8 | 90.5% | 186 | 49.8% |

| Sample | ng/cm^2 | % Decrease | ng/cm^2 | % Decrease |
|---|---|---|---|---|
| TPU2 | 7.37 | | 28.0 | |
| Film 2 | 3.06 | 58.5% | 9.05 | 67.7% |
| TPU4 | 68.1 | | 227.3 | |

TABLE 4-continued

| BSA and Fibrinogen absorption data from fluorescence method | | | | |
|---|---|---|---|---|
| Film6 | 5.07 | 93% | 23.9 | 89% |
| PVC | 87.1 | | 233 | |
| Film 6 | 4.0 | 95% | 10.5 | 95% |
| Pebax | 73.1 | | 268 | |
| Film 7 | 2.0 | 97% | 17.3 | 94% |
| PA 11 | 66.3 | | 225 | |
| Film 8 | 15.7 | 76% | 102.4 | 54% |

< Detection Limit (BSA = 5 ng/cm$^2$ and Fbg = 30 ng/cm$^2$)
Detection Limit for BSA is less than 5 ng/cm$^2$, for Fbg is less than 30 ng/cm$^2$.
Negative control is pure TPU without any additives.
Positive control are SDS washed samples to ensure 100% removal of absorbed proteins.

Annealing

An extruded or compression molding sample of a Film from Table 1 is hung inside an oven by a binder clip. The oven is heated to a temperature of 80° C. and held for a period up to 48 hours. Samples were removed after 24 hour periods and protein adsorption measured. Results of annealing of the samples on protein adsorption are presented in Table 5 below:

TABLE 5

| Annealing effect | | |
|---|---|---|
| Formulation | BSA reduction | Fbg reduction |
| INV EX 3 1% TPU3, 0 day anneal | 42% | 71% |
| INV EX 3 1% TPU3, 1 day anneal | 86% | 85% |
| INV EX 3 1% TPU3, 2 day anneal | 92% | 96% |
| INV EX 3 2.5% TPU3, 0 day anneal | 95% | 88% |
| INV EX 3 2.5% TPU3, 1 day anneal | 98% | 92% |
| INV EX 3 2.5% TPU3, 2 day anneal | 100% | 96% |

*A negative reduction values means the sample shows increased protein adsorption.

As can been seen in Table 5, the amount of protein adsorbed onto the surface of the Films containing the inventive additives following annealing of the Film is significantly reduced compared to a Film containing the inventive additives which has not been subjected to the annealing process.

Each of the documents referred to above is incorporated herein by reference, including any prior applications, whether or not specifically listed above, from which priority is claimed. The mention of any document is not an admission that such document qualifies as prior art or constitutes the general knowledge of the skilled person in any jurisdiction. Except in the Examples, or where otherwise explicitly indicated, all numerical quantities in this description specifying amounts of materials, reaction conditions, molecular weights, number of carbon atoms, and the like, are to be understood as modified by the word "about." It is to be understood that the upper and lower amount, range, and ratio limits set forth herein may be independently combined. Similarly, the ranges and amounts for each element of the technology described herein can be used together with ranges or amounts for any of the other elements.

As described hereinafter the molecular weight of the materials described above have been determined using known methods, such as GPC analysis using polystyrene standards. Methods for determining molecular weights of polymers are well known. The methods are described for instance: (i) P. J. Flory, "Principles of star polymer Chemistry", Cornell University Press 91953), Chapter VII, pp 266-315; or (ii) "Macromolecules, an Introduction to star polymer Science", F. A. Bovey and F. H. Winslow, Editors, Academic Press (1979), pp 296-312. As used herein the weight average and number weight average molecular weights of the materials described are obtained by integrating the area under the peak corresponding to the material of interest, excluding peaks associated with diluents, impurities, uncoupled star polymer chains and other additives.

As used herein, the transitional term "comprising," which is synonymous with "including," "containing," or "characterized by," is inclusive or open-ended and does not exclude additional, un-recited elements or method steps. However, in each recitation of "comprising" herein, it is intended that the term also encompass, as alternative embodiments, the phrases "consisting essentially of" and "consisting of," where "consisting of" excludes any element or step not specified and "consisting essentially of" permits the inclusion of additional un-recited elements or steps that do not materially affect the basic and novel characteristics of the composition or method under consideration. That is "consisting essentially of" permits the inclusion of substances that do not materially affect the basic and novel characteristics of the composition under consideration.

While certain representative embodiments and details have been shown for the purpose of illustrating the subject technology described herein, it will be apparent to those skilled in this art that various changes and modifications can be made therein without departing from the scope of the subject invention. In this regard, the scope of the technology described herein is to be limited only by the following claims.

What is claimed is:

1. A surface-modified polymer composition comprising:
   a) a surface modifying additive composition comprising an oligomeric or polymeric additive formed from two or more monomers selected from the group consisting of:
      i) a polyalkylene glycol monomer;
      ii) a silicone or fluorocarbon monomer, or combinations thereof; or
      iii) an alkyl substituted methacrylate, acrylate, or combinations thereof, wherein said alkyl substituted methacrylate and acrylate is selected from methyl methacrylate, ethyl acrylate, ethyl methacrylate, hydroxypropyl methacrylate, 2-hydroxyethyl methacrylate, cyclohexyl methacrylate, 3-chloro-2-hydroxypropyl methacrylate, hydroxypropyl methacrylate, phenyl methacrylate, benzyl methacrylate, 2-naphthyl methacrylate, 2-(trimethylsilyloxy)-ethylmethacrylate, 3-(trichlorosilyl)propyl methacrylate, 3-(trimethoxysilyl)-propyl methacrylate, 3-[tris(trimethylsiloxy)silyl]propyl methacrylate, trimethylsilyl methacrylate, allyl methacrylate, vinyl methacrylate, 3-(diethoxymethylsilyl)propyl methacrylate, 3-(dimethylchlorosilyl)propyl methacrylate, 3-chloro-2-hydroxypropyl methacrylate, and 2-hydroxypropyl 2-(methacryloyloxy)ethyl phthalate, wherein the oligomeric or polymeric additive is a random polymer or copolymer; and
   b) a base polymer selected from nylon, a polyethylene, a thermoplastic polyurethane, a polyvinylchloride, a polysulfone, a polysiloxane, a polypropylene, a polycarbonate, a polyether sulfone, a polyether ether ketone, a polylactide (PLA) polymer, a polylactide-co-glycolide (PLG) polymer, a polycaprolactone polymer, a polydioxanol polymer, a poly(1,3-trimethylene carbonate) polymer, a polytyrosine carbonate polymer, a polyacrylate, a polymethacrylate, polylactic acid, polyglycolic acid, and combinations thereof;

wherein the oligomeric or polymeric additive (a) is incorporated into the base polymer (b) to form a blend.

2. The surface-modifying polymer composition of claim 1, wherein the silicone or fluorocarbon monomer is present in the oligomeric or polymeric additive in an amount from 5 wt % to 40 wt % of total the monomer composition.

3. The surface-modifying polymer composition of claim 2, wherein the silicone monomer comprises a functionalized polysiloxane.

4. The surface-modifying polymer composition of claim 1 wherein the fluorocarbon monomer includes a functionalized fluorocarbon.

5. The surface-modifying polymer composition of claim 1, wherein the polyaklyene glycol monomer is present in the oligomeric or polymeric additive in an amount from 10 wt % to 50 wt % of the total monomer composition.

6. The surface-modifying polymer composition of claim 5, wherein the polyalkylene glycol monomer is a monomethyl polyethylene glycol methacrylate.

7. The surface-modifying polymer composition of claim 1, wherein the alkyl substituted methacrylate, acrylate, acrylamide or vinyl monomer is present in the oligomeric or polymeric additive in an amount from 10 wt % to 70 wt % of the total monomer composition.

8. The surface-modifying polymer composition of claim 7, wherein the alkyl substituted methacrylate, acrylate, acrylamide or vinyl monomer comprises methyl methacrylate.

9. The surface-modifying polymer composition of claim 1, wherein the additive composition has a molecular weight (Mn) of from 1000 to 50,000 daltons.

10. The surface-modifying polymer composition of claim 1, wherein the additive composition provides a reduction in protein absorption of at least 50 percent.

11. The surface modified polymer composition of claim 1, wherein the base polymer comprises thermoplastic polyurethane.

12. The surface modified polymer composition of claim 1, further comprising one or more additional thermoplastic polyurethanes to form a thermoplastic polyurethane blend.

13. The surface modified polymer composition of claim 1, wherein the surface modified polymer composition is non-protein fouling, non-thrombogenic, or combinations thereof.

14. An article including a surface modifying polymer composition, the surface modifying polymer composition comprising:
  a) an oligomeric or polymeric additive formed from two or more monomers selected from the group consisting of:
    i) polyalkylene glycol monomer;
    ii) a silicone or fluorocarbon monomer, or combinations thereof; or
    iii) an alkyl substituted methacrylate, acrylate, or combinations thereof, wherein said alkyl substituted methacrylate and acrylate is selected from methyl methacrylate, ethyl acrylate, ethyl methacrylate, hydroxypropyl methacrylate, 2-hydroxyethyl methacrylate, cyclohexyl methacrylate, 3-chloro-2-hydroxypropyl methacrylate, hydroxypropyl methacrylate, phenyl methacrylate, benzyl methacrylate, 2-naphthyl methacrylate, 2-(trimethylsilyloxy)-ethylmethacrylate, 3-(trichlorosilyl)propyl methacrylate, 3-(trimethoxysilyl)-propyl methacrylate, 3-[tris(trimethylsiloxy)silyl]propyl methacrylate, trimethylsilyl methacrylate, allyl methacrylate, vinyl methacrylate, 3-(diethoxymethylsilyl)propyl methacrylate, 3-(dimethylchlorosilyl)propyl methacrylate, 3-chloro-2-hydroxypropyl methacrylate, and 2-hydroxypropyl 2-(methacryloyloxy)ethyl phthalate, wherein the oligomeric or polymeric additive is a random polymer or copolymer; and
  b) a base polymer selected from nylon, a polyethylene, a thermoplastic polyurethane, a polyvinylchloride, a polysulfone, a polysiloxane, a polypropylene, a polycarbonate, a polyether sulfone, a polyether ether ketone, a polylactide (PLA) polymer, a polylactide-co-glycolide (PLG) polymer, a polycaprolactone polymer, a polydioxanol polymer, a poly(1,3-trimethylene carbonate) polymer, a polytyrosine carbonate polymer, a polyacrylate, a polymethacrylate, polylactic acid, polyglycolic acid, and combinations thereof;
  wherein the oligomeric or polymeric additive (a) is incorporated into the base polymer (b) to form a blend.

15. The article of claim 14, wherein the article comprises a medical device.

16. The article of claim 15, wherein the medical device comprises one or more of an angiography catheter, an angioplasty catheter, a urology catheters, a dialysis catheter, a Swan-Ganz catheter, a central venous catheter, a peripherally inserted central catheter, a catheter connector, a dialysis membrane, medical tubing, a wound are article, and orthopedic article, a neural implant, a film, a drape, a biosensor, a dental implant, a heart valve, a heart by-pass machine, an extracorporeal blood device, a nerve conduit, a vascular graft, a stent, an implant or a contact lens.

17. The article of claim 16, wherein the wound care article comprises one or more of a wound closure, a staple, a suture, a mesh, a buttressing device, a suture reinforcement, or a wound care dressing.

18. The article of claim 16 wherein the orthopedic article comprises one or more of a nail, a screw, a plate, a cage, or a prosthetic.

19. The article of claim 16, wherein the neural implant comprises one or more of a drain or a shunt.

20. The article of claim 16, wherein the implant comprises one or more of an ocular implant, a cochlear implant, or a breast implant.

21. The article of claim 14, wherein the article is a personal care article, a pharmaceutical article, a health care product article, or a marine article.

22. A method of making the article of claim 14, comprising:
  a) making a surface-modifying polymer composition; and
  b) forming the article.

* * * * *